(12) United States Patent
Ouchi et al.

(10) Patent No.: US 6,860,516 B2
(45) Date of Patent: Mar. 1, 2005

(54) CHANNEL TUBE COUPLING STRUCTURE FOR ANTI-POLLUTION TYPE ENDOSCOPE

(75) Inventors: Teruo Ouchi, Saitama (JP); Kazuyuki Yamamoto, Tokyo (JP)

(73) Assignee: PENTAX Corporation, Tokyo (JP)

( * ) Notice: Subject to any disclaimer, the term of this patent is extended or adjusted under 35 U.S.C. 154(b) by 65 days.

(21) Appl. No.: 10/309,147

(22) Filed: Dec. 4, 2002

(65) Prior Publication Data

US 2003/0122374 A1 Jul. 3, 2003

(30) Foreign Application Priority Data

Dec. 7, 2001 (JP) ................................. P2001-373514
Jan. 7, 2002 (JP) ................................. P2002-000245

(51) Int. Cl.[7] ................................................ F16L 39/00
(52) U.S. Cl. .......................... 285/124.1; 285/120.1; 600/121; 600/123; 600/153; 600/156; 600/158
(58) Field of Search ................................. 600/121, 123, 600/124, 125, 153, 156, 158; 285/120.1, 124.1, 124.2, 124.3, 124.4, 124.5

(56) References Cited

U.S. PATENT DOCUMENTS

| 4,991,564 | A |   | 2/1991 | Takahashi et al. | |
|---|---|---|---|---|---|
| 5,292,305 | A | * | 3/1994 | Boudewijn et al. | 604/43 |
| 5,630,787 | A | * | 5/1997 | Yabe et al. | 600/121 |
| 6,110,104 | A | * | 8/2000 | Suzuki et al. | 600/124 |
| 6,520,951 | B1 | * | 2/2003 | Carrillo et al. | 604/516 |
| 6,579,279 | B1 | * | 6/2003 | Rabiner et al. | 604/528 |
| 6,620,139 | B1 | * | 9/2003 | Plicchi et al. | 604/264 |

FOREIGN PATENT DOCUMENTS

| JP | 329634 | 2/1991 |
|---|---|---|
| JP | 2750612 | 2/1998 |
| JP | 2750613 | 2/1998 |
| JP | 3017573 | 12/1999 |

OTHER PUBLICATIONS

English Language Translation for JP Appln. No. 3–017573.

* cited by examiner

*Primary Examiner*—James M. Hewitt
(74) *Attorney, Agent, or Firm*—Greenblum & Bernstein, P.L.C.

(57) ABSTRACT

A channel tube coupling structure for an anti-pollution type endoscope which can easily and smoothly couple a multi-lumen type channel tube extending from a base end of an outer sheath with tubes on a side of the endoscope and separate the multi-lumen type channel tube therefrom. At a side surface in a vicinity of the base end of the channel tube, side holes communicate with a plurality of tubes that are formed so as to be shifted from one another in an axial direction. A coupling hole, where the base end portion of the channel tube is loosely inserted thereinto and freely removed therefrom, provides a space in a radial direction between the channel tube and the coupling hole. Annular sealing members are provided which seal portions between the respective side holes, in a state where the base end portion of the channel tube is inserted into the coupling hole. Respective holes on the endoscope side are opened and coupled at the inner peripheral surface of the coupling hole at portions along the annular sealing members.

10 Claims, 7 Drawing Sheets

CHANNEL TUBE COUPLING STRUCTURE FOR ANTI-POLLUTION TYPE ENDOSCOPE

BACKGROUND OF THE INVENTION

The present invention relates to a channel tube coupling structure for an anti-pollution type endoscope having an insertion portion to which an outer sheath is detachably attached.

In order to prevent the insertion portion of the endoscope to be inserted within a human body from being polluted by polluted liquid within the human body, it is necessary not only to cover the insertion portion of the endoscope by an outer sheath but also to provide, in the outer sheath, a channel tube communicating with the interior of the human body so that fluid, a treatment instrument etc. can pass through the channel tube.

Such a channel tube is inserted into and disposed within the outer sheath which is arranged to cover the insertion portion of the endoscope so as to be detachable freely. Further, the channel tube is configured in a manner that the base end portion thereof extending from the base end of the outer sheath is freely coupled with and separated from tubes on the endoscope.

The endoscope is required to have various kinds of tubes such as an air supply tube, a water supply tube, a suction tube (also serves as a tube for passing a treatment member therethrough) etc. Thus, it is convenient as the aforesaid channel tube to employ a so-called multi-lumen tube in which a plurality of tubes are formed in parallel in the axial direction (see Japanese Patent Laid-Open No. 29634/1991 etc.).

However, when such a multi-lumen tube is employed as the channel tube, the coupling direction and the operation number of time for coupling with and separating from the tubes on the endoscope (for example, the air supply tube, the water supply tube, the suction tube) become plural, so that the procedures for the coupling and separation of the tubes becomes troublesome.

Accordingly, an object of the invention is to provide a channel tube coupling structure for an anti-pollution type endoscope which can easily and smoothly couple a multi-lumen type channel tube extending from the base end of an outer sheath with tubes on the endoscope and separate the multi-lumen type channel tube therefrom.

SUMMARY OF THE INVENTION

In order to attain the aforesaid object, a channel tube coupling structure for an anti-pollution type endoscope according to the invention is arranged in a manner that a plurality of tubes are formed in parallel in an axial direction within a channel tube that is inserted into and disposed within an outer sheath being detachably attached to and covering an insertion portion of the endoscope. The plurality of tubes are freely coupled to and separated from corresponding endoscope side tubes at a base end portion of the channel tube extending from a base end side of the outer sheath, respectively. At a side surface in a vicinity of the base end of the channel tube, side holes respectively communicating with the plurality of tubes are formed so as to be shifted from one another in an axial direction. Within a coupling hole where the base end portion of the channel tube is loosely inserted thereinto and removed therefrom freely so as to provide a space in a radial direction between the channel tube and the coupling hole, annular sealing members are provided which seal portions between the respective side holes in a state where the base end portion of the channel tube is inserted into the coupling hole. The endoscope side holes are opened at an inner peripheral surface of the coupling hole, and located at portions between the annular sealing members, respectively.

When a cross sectional area of a flow path at the space formed between an outer peripheral surface of the channel tube and the coupling hole is larger than a cross sectional area of each of the tubes formed within the channel tube, a flow rate at the time of coupling is scarcely influenced even if the channel tube is in any rotating state with respect to the coupling hole.

The invention also provides a channel tube coupling structure for an anti-pollution type endoscope, which is arranged in a manner that a plurality of tubes are formed in parallel in a axial direction within a channel tube that is inserted into and disposed within an outer sheath being detachably attached to and covering an insertion portion of the endoscope. The plurality of tubes are freely coupled to and separated from corresponding endoscope side tubes at a base end portion of the channel tube extending from a base end side of the outer sheath, respectively. At a side surface in a vicinity of the base end of the channel tube, side holes respectively communicating with the plurality of tubes are formed so as to be shifted from one another in a axial direction. End portion openings of the plurality of endoscope side tubes corresponding to the plurality of tubes of the channel tube are formed at positions corresponding to side holes of the channel tube on an inner peripheral surface of the coupling hole where the channel tube is inserted thereinto and drawn therefrom freely, respectively.

Further, when the end portion openings of the endoscope side tubes are formed each to have a circumferential groove shape along an entire circumference of an inner peripheral surface of the coupling hole, the respective tubes can be coupled surely even if the channel tube is in any rotation state around an axis.

The present disclosure relates to the subject matter contained in Japanese patent application No. P2001-373514 (filed on Dec. 7, 2001) and P2002-000245 (filed on Jan. 7, 2002), which are expressly incorporated herein by reference in their entireties.

DESCRIPTION OF THE PREFERRED EMBODIMENT

The embodiments of the invention will be explained with reference to the accompanying drawings.

Figure 6:
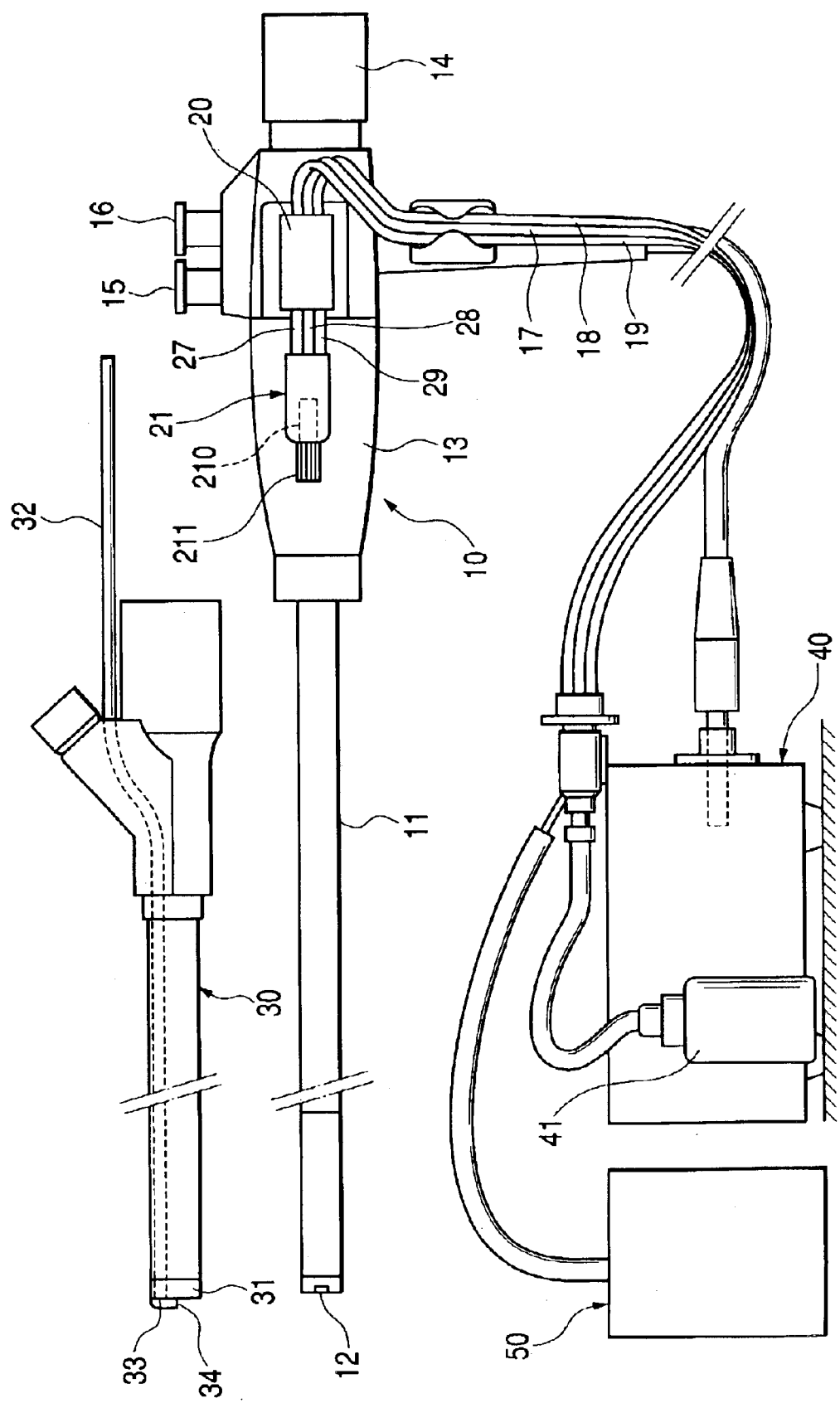
FIG. 6 is an external view of the side surface of the entire system in a state where the insertion portion of the anti-pollution type endoscope according to the embodiment of the invention is not covered by an outer sheath.
Figure 7:
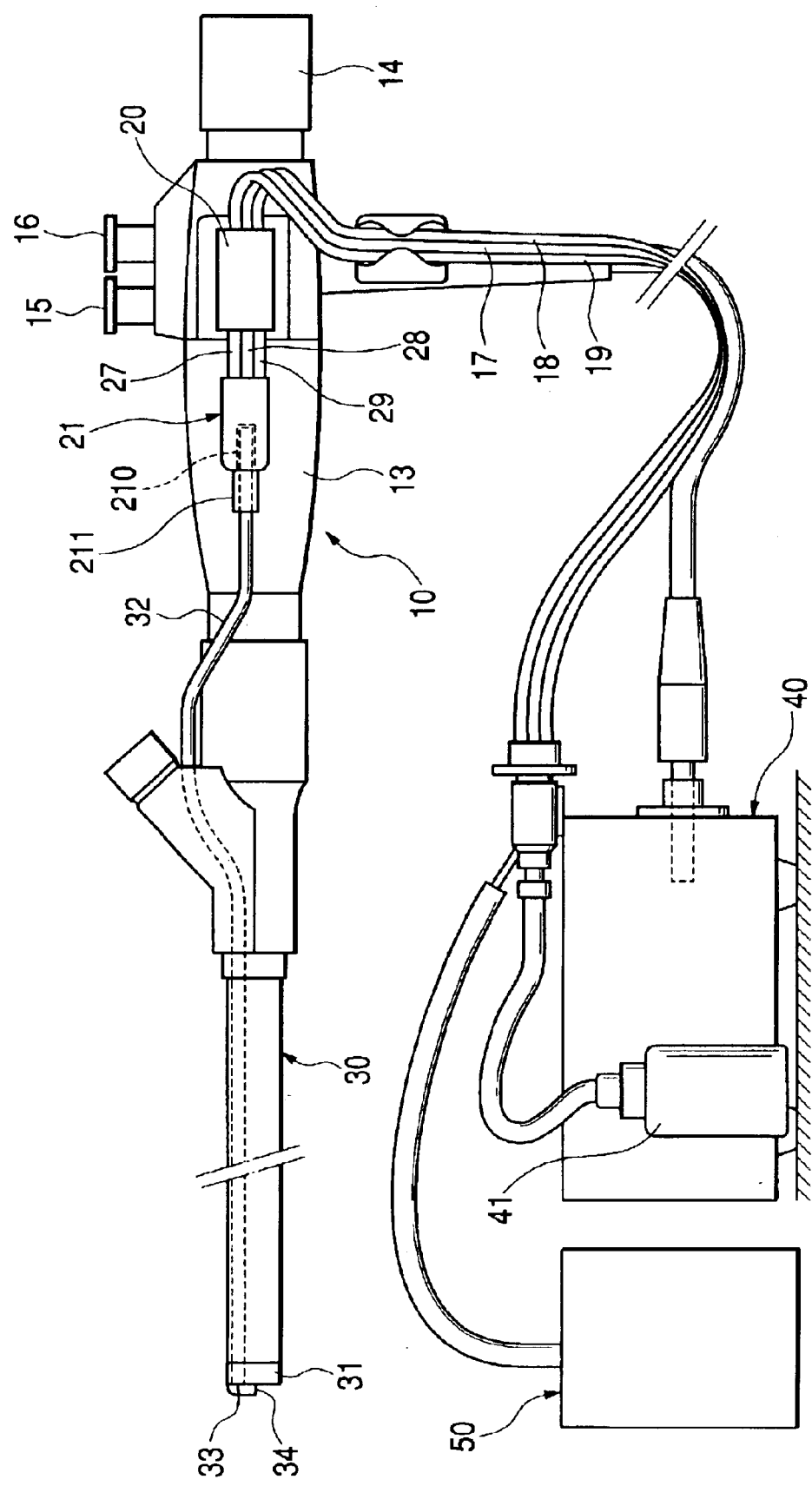
FIG. 7 is an external view of the side surface of the entire system in a state where the insertion portion of the anti-pollution type endoscope according to the embodiment of the invention is covered by the outer sheath.

FIGS. 6 and 7 show the entire configuration of the system of an anti-pollution type endoscope. FIG. 6 shows a state where an insertion portion 11 of an endoscope 10 is not covered by an outer sheath 30. FIG. 7 shows a state where the insertion portion 11 of the endoscope 10 is covered by the outer sheath 30.

The insertion portion 11 of the endoscope 10 is configured in a flexible tubular shape. An observation window 12 and a not-shown illumination window etc. are disposed at the tip end of the insertion portion 11. An operation portion 13 is coupled to the base end of the insertion portion 11.

A transparent tip end cap 31 is attached to the tip end portion of the outer sheath 30 which is detachably attached to the insertion portion 11 to cover the insertion portion 11. A suction port 33 and an air/water supply nozzle port 34 are opened at the surface of the tip end cap 31.

A channel tube 32 in the form of a so-called a multi-lumen tube is inserted and disposed within the outer sheath 30 over the entire length thereof, and the base end portion of the channel tube 32 is extended from the base end side of the outer sheath 30.

Figure 8:
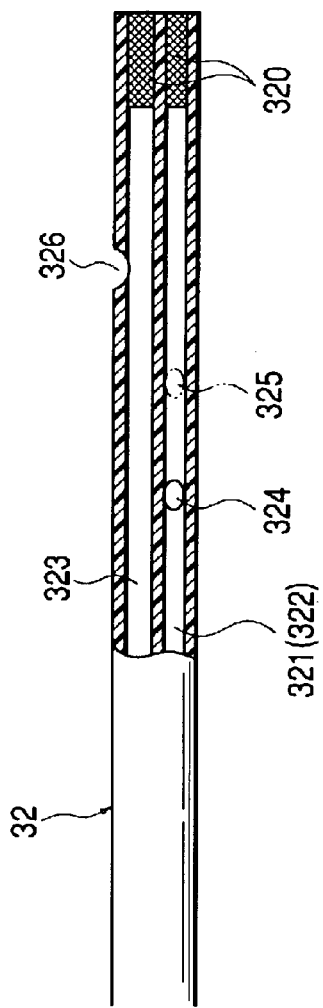
FIG. 8 is a sectional view of the side surface at a portion in the vicinity of the base end of the channel tube of the anti-pollution type endoscope according to the embodiment of the invention.

The outer shape of the channel tube 32 is circular in section. As shown in FIG. 8, within the channel tube, three tubes, that is, an air supply tube 321 and a water supply tube 322 each communicating with the air/water supply nozzle port 34 and a suction tube 323 communicating with the suction port 33 are formed in parallel in the axial direction. Each of the base ends of the air supply tube 321, the water supply tube 322 and the suction tube 323 is blocked by a blocking plug member 320.

At the side surface in the vicinity of the base end of the channel tube 32, side holes (an air supply side hole 324, a water supply side hole 325 and a suction side hole 326) respectively communicating with the air supply tube 321, the water supply tube 322 and the suction tube 323 are formed so as to be opened and shifted from one another in the axial direction.

When the insertion portion 11 is covered by the outer sheath 30, the base end portion of the channel tube 32 is inserted into and coupled with the coupling hole 210 of the tube connector 21 described later.

Returning to FIGS. 6 and 7, at the operation portion 13 of the endoscope 10, there are disposed an eye piece portion 14 for enlarging an image observed by the endoscope which is transmitted through an image guide fiber bundle, an air/water supply operation valve 15 for performing an air/water supply operation, and a suction operation valve 16 for performing a suction operation, etc.

Reference numerals 17, 18 and 19 depict air supply and water supply tubes and a suction tube which are coupled to the air/water supply operation valve 15 and the suction operation valve 16, respectively, through a coupling adapter 20 detachably attached to the operation portion 13. Such a coupling adapter 20 is described in Japanese Patent Laid-Open No. 354928/1992 etc.

The base ends of the air supply tube 17 and the water supply tube 18 are coupled to an air/water supply device 41 provided at a light source device 40. The base end portion of the suction tube 19 is coupled to an external suction device 50 so as to be communicated therewith.

An air supply coupling tube 27, a water supply coupling tube 28 and a suction coupling tube 29 respectively communicating with the air/water supply operation valve 15 and the suction operation valve 16 are extended from the coupling adapter 20. A tube connector 21 attached to the tip ends of the air supply coupling tube 27, the water supply coupling tube 28 and the suction coupling tube 29 is disposed along the side surface of the operation portion 13.

The tube connector 21 is provided with a coupling hole 210 where the base end portion of the channel tube 32 is inserted thereinto and removed therefrom. At the inlet portion of the coupling hole 210, a tube fixing fastening pipe 211 is disposed for fixing the channel tube 32 inserted into the coupling hole 210 so as not to be detached from the tube connector 21.

Figure 1:
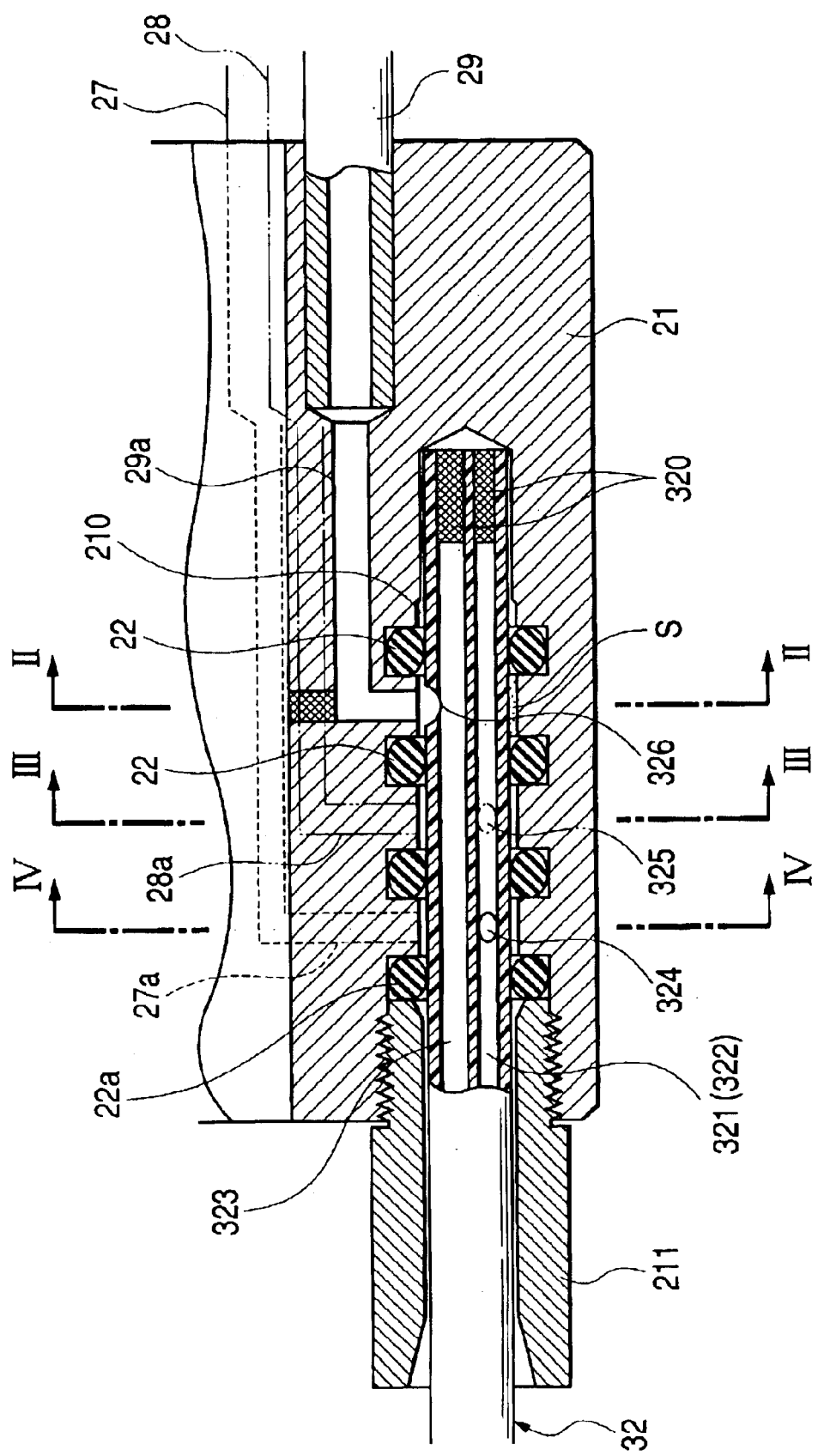
FIG. 1 is a side sectional view of the tube connector of an anti-pollution type endoscope according to an embodiment of the invention.
Figure 2:
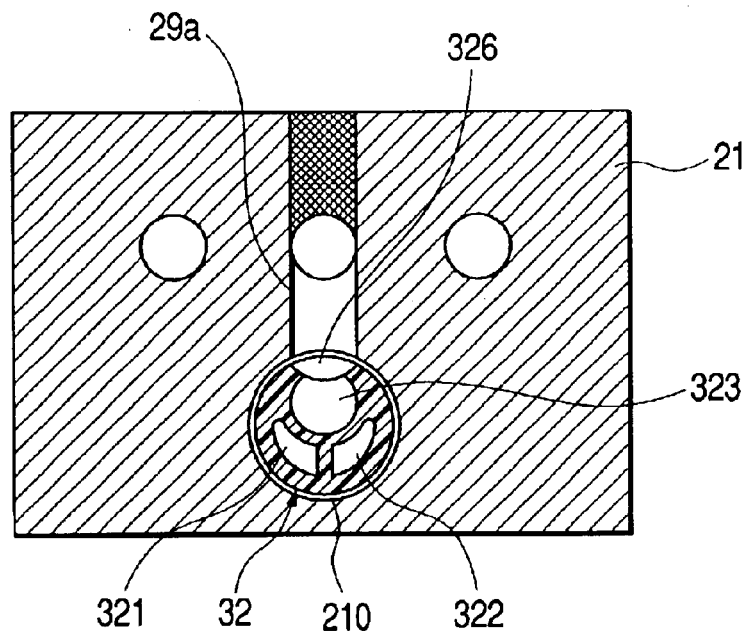
FIG. 2 is a sectional view along a line II—II in FIG. 1 of the tube connector of the anti-pollution type endoscope according to the embodiment of the invention.
Figure 3:
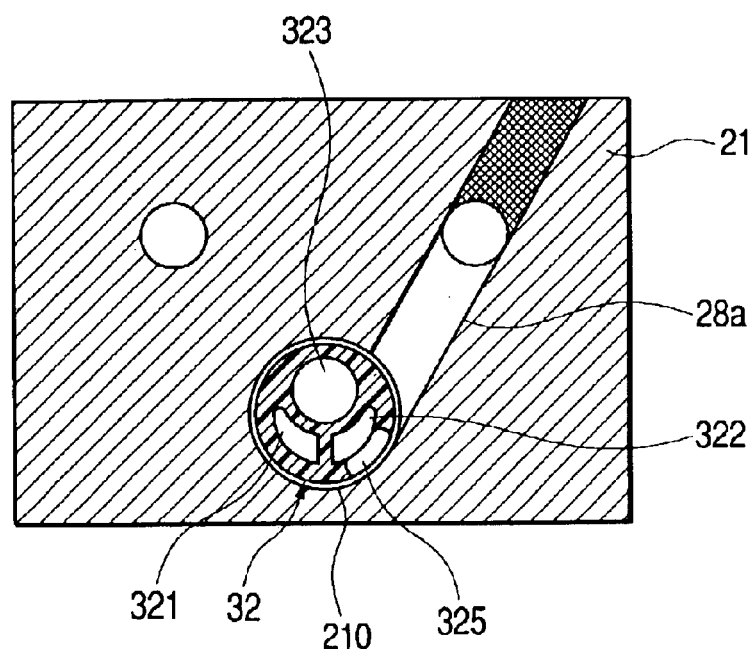
FIG. 3 is a sectional view along a line III—III in FIG. 1 of the tube connector of the anti-pollution type endoscope according to the embodiment of the invention.
Figure 4:
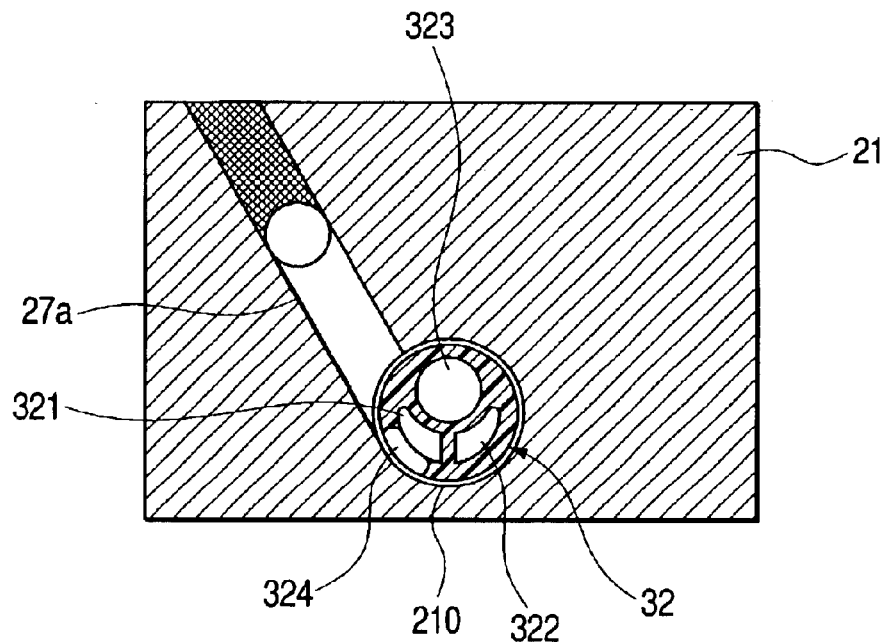
FIG. 4 is a sectional view along a line VI—VI in FIG. 1 of the tube connector of the anti-pollution type endoscope according to the embodiment of the invention.

FIG. 1 shows a state where the base end portion of the channel tube 32 extending from the outer sheath 30 is coupled to the tube connector 21 of the endoscope 10. FIGS. 2, 3 and 4 show sectional diagrams taken along a line II—II, a line III—III and a line IV—IV in FIG. 1, respectively.

The tip ends of the air supply coupling tube 27, the water supply coupling tube 28 and the suction coupling tube 29 are inserted into the tube connector 21 from the one end side thereof and fixed thereto. At the other end side of the tube connector, a coupling hole 210 is formed so as to provide a space in the radial direction between the channel tube 32 and the coupling hole 210 so that the base end portion of the channel tube 32 is loosely inserted thereinto and removed therefrom freely.

In a state where the channel tube 32 is inserted into the coupling hole 210, all of the air supply side hole 324, the water supply side hole 325 and the suction side hole 326 formed at the channel tube 32 are inserted within the coupling hole 210.

Within a plurality of annular grooves formed at the inner peripheral surface of the coupling hole 210, O rings 22 (annular sealing members) are attached which hermetically seal portions between the corresponding adjacent ones of the side holes 324, 325 and 326 respectively in a state where the base end portion of the channel tube 32 is fully inserted into a position abutting against the bottom surface of the coupling hole 210.

An air supply communicating hole 27a, a water supply communicating hole 28a and a suction communicating hole 29a are formed in the tube connector 21 so as to communicate with the air supply coupling tube 27, the water supply coupling tube 28 and the suction coupling tube 29. The air supply communicating hole 27a, the water supply communicating hole 28a and the suction communicating hole 29a are opened at the inner peripheral surface of the coupling hole 210 and located at the positions between the corresponding ones of the O rings 22, respectively.

As a result, when the base end portion of the channel tube 32 is fully inserted into the coupling hole 210 of the tube connector 21, the air supply tube 321, the water supply tube 322 and the suction tube 323 are made communicate simultaneously by the single operation with the air supply coupling tube 27, the water supply coupling tube 28 and the suction coupling tube 29 through the air supply side hole 324, the water supply side hole 325 and the suction side hole 326, respectively. When the channel tube 32 is pulled in the reverse direction, the channel tube 32 is removed from the coupling hole 210 and consequently, the aforesaid communicating state is cancelled simultaneously by the single operation.

Figure 5:
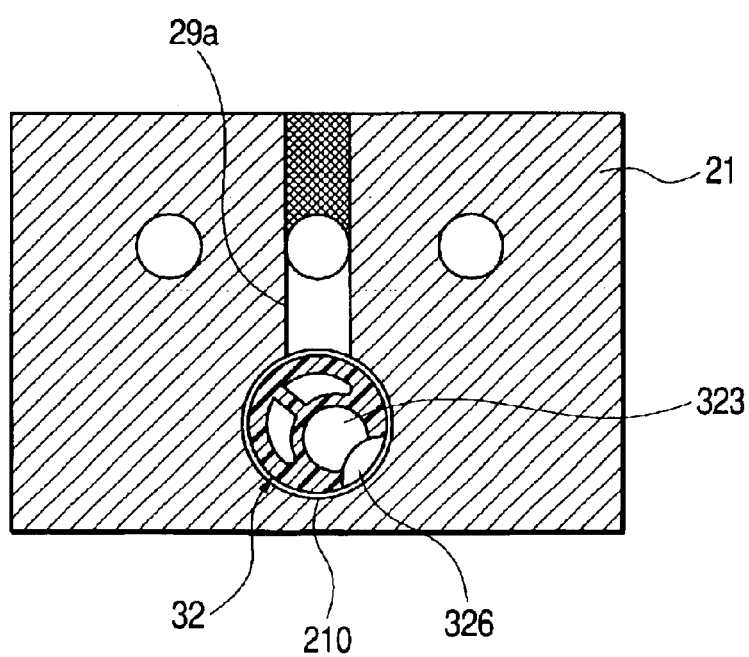
FIG. 5 is a sectional view along the line II—II of the tube connector of the anti-pollution type endoscope according to the embodiment of the invention in a coupling state where the channel tube is rotated.

Further, the channel tube 32 is rotatable freely around the axis thereof when inserted into the coupling hole 210. As FIG. 5 exemplarily shows a communicating state (the same sectional view as that taken along the line II—II) between the suction tube 323 and the suction communicating hole 29a, a communicating state (coupling state) between each tube 321, 322, 323 and the corresponding hole 27a, 28a, 29a can be established suitably through the space between the outer peripheral surface of the channel tube 32 and the coupling hole 210 even if the channel tube 32 is in any rotation state around the axis.

To this end, a cross sectional area of a flow path (S shown in FIG. 1) at the space between the outer peripheral surface of the channel tube 32 and the coupling hole 210 is desirably larger than any cross sectional area of the air supply tube 321, the water supply tube 322 and the suction tube 323.

The channel tube 32 inserted into the coupling hole 210 in this manner can be removed out easily from the coupling hole 210 when being pulled by a hand. However, when the tube fixing fastening pipe 211 engaged with the inlet portion of the coupling hole 210 is fastened, the O ring 22a at the outer end portion is deformed and pressed against the surface of the channel tube 32, whereby the channel tube 32 is fixed to the tube connector 21.

Figure 9:
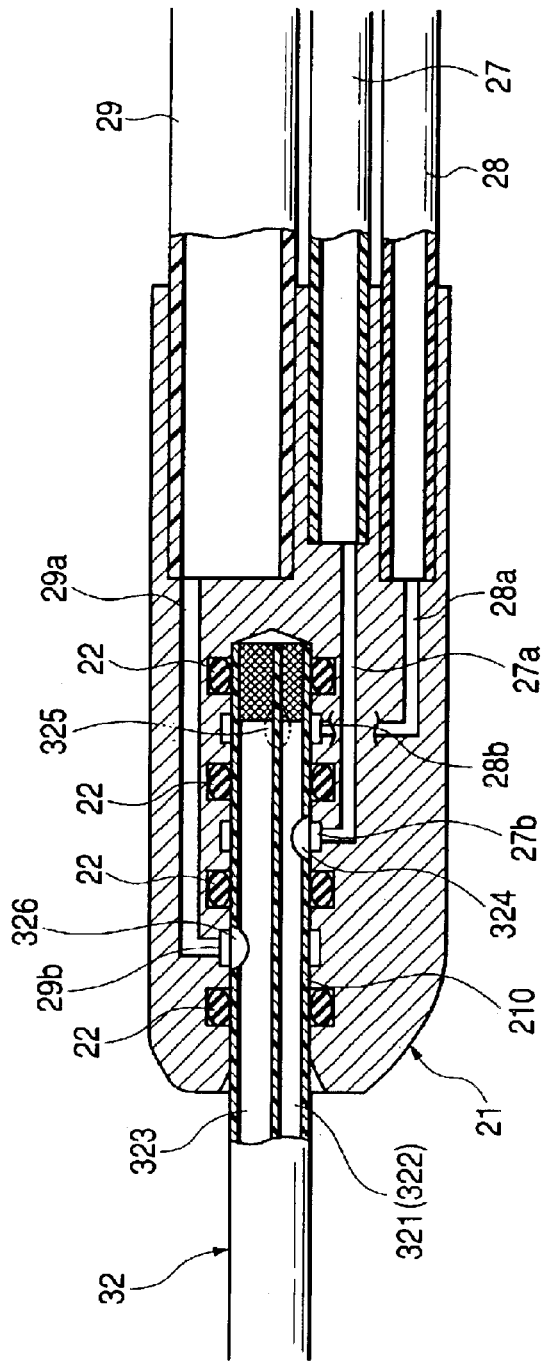
FIG. 9 is a side sectional view of the tube connector of an anti-pollution type endoscope according to a second embodiment of the invention.
Figure 10:
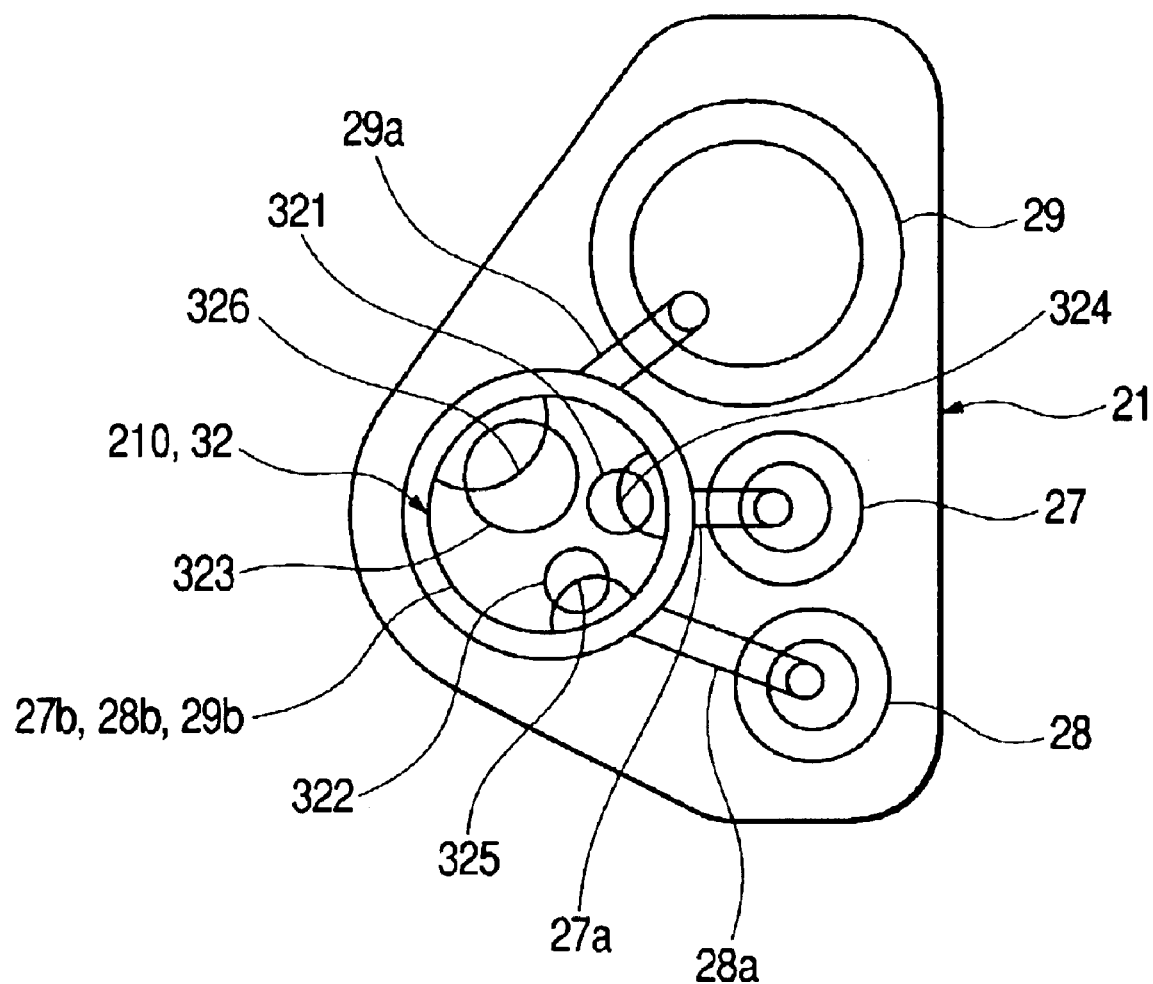
FIG. 10 is a front perspective view of the tube connector of the anti-pollution type endoscope according to the second embodiment of the invention.

FIGS. 9 and 10 show a second embodiment of the present invention. In the second embodiment, an air supply path end portion opening 27b, a water supply path end portion opening 28b and a suction path end portion opening 29b, each having an annular groove shape, is formed at the inner peripheral surface of the coupling hole 210. The air supply path end portion opening 27b, the water supply path end portion opening 28b and the suction path end portion opening 29b extends along the entire circumference of the coupling hole, and located at positions facing to the air supply side hole 324, the water supply side hole 325 and the suction side hole 326, respectively, in a state where the tip end of the channel tube 32 is fully inserted into a position abutting against the bottom surface of the coupling hole 210.

Such the air supply path end portion opening 27b, the water supply path end portion opening 28b and the suction path end portion opening 29b are communicated with the air supply coupling tube 27, the water supply coupling tube 28 and the suction coupling tube 29 through the air supply communication hole 27a, the water supply communication hole 28a and the suction communication hole 29a, respectively.

The O rings 22 for sealing are attached on the inner peripheral surface of the coupling hole 210 at such positions that each of the air supply path end portion opening 27b, the water supply path end portion opening 28b and the suction path end portion opening 29b is sandwiched by the adjacent O rings, thereby to prevent fluid from leaking from a space between the inner peripheral surface of the coupling hole 210 and the outer peripheral surface of the channel tube 32.

Thus, when the channel tube 32 is fully inserted into the coupling hole 210 of the tube connector 21, the air supply tube 321, the water supply tube 322 and the suction tube 323 are made communicate simultaneously by the single operation with the air supply coupling tube 27, the water supply coupling tube 28 and the suction coupling tube 29 through the air supply side hole 324, the water supply side hole 325 and the suction side hole 326, respectively, even if the channel tube 32 is in any rotation state around the axis. When the channel tube 32 is pulled in the reverse direction, the channel tube 32 is removed from the coupling hole 210 and consequently the aforesaid communicating state is cancelled simultaneously by the single operation.

The invention is not limited to the aforesaid embodiment, and the number of tubes disposed within the channel tube 32 may be two, for example, and alternatively may be four or more.

As described above, according to the invention, by merely inserting the base end portion of the channel tube into the coupling hole, the plurality of the tubes within the channel tube extending from the base end of the outer sheath are coupled and communicated with the endoscope side tubes through the space formed between the outer peripheral surface of the channel tube and the coupling hole, whereby a plurality of the tubes can be smoothly and easily coupled with and separated from the endoscope side tubes by the single operation even if the channel tube is in any rotation state.

Further, according to the invention, at the side surface in the vicinity of the base end of the multi-lumen type channel tube extending from the base end of the outer sheath, the side holes respectively communicating with the plurality of tubes of the channel tube are formed so as to be shifted from one another in an axial direction. The end portion openings of the plurality of endoscope side tubes corresponding to the plurality of tubes of the channel tube are formed at the positions corresponding to the side holes of the channel tube on the inner peripheral surface of the coupling hole where the channel tube is inserted thereinto and removed therefrom freely, respectively. Thus, the channel tube of the outer sheath can be coupled to and separated from the endoscope side tubes easily and smoothly by the single operation.

Further, when the end portion openings of the endoscope side tubes are formed each to have the annular groove shape along the entire circumference of the inner peripheral surface of the coupling hole, the respective tubes can be coupled surely even if the channel tube is in any rotation state around the axial.

What is claimed is:

1. In a channel tube coupling structure for an anti-pollution endoscope in which a plurality of tubes extend in parallel in an axial direction within a channel tube that is disposed within an outer sheath that is detachably attached to and covers an insertion portion of the endoscope, and the plurality of tubes are freely coupled to and separated from corresponding endoscope side tubes respectively at a base end portion of the channel tube extending from a base end of the outer sheath, the channel tube coupling structure for the anti-pollution endoscope comprising:

side holes respectively communicate with the plurality of tubes, and are formed at a side surface in a vicinity of the base end portion of the channel tube, the side holes being staggered with respect to one another in a axial direction;

a coupling hole where the base end portion of the channel tube is loosely inserted thereinto and drawn freely therefrom so as to provide a space in a radial direction between the channel tube and the coupling hole; and annular sealing members, provided within the coupling hole, that seal portions between the respective side holes when the base end portion of the channel tube is inserted into the coupling hole;

wherein the endoscope side holes are opened at an inner peripheral surface of the coupling hole, and located at portions between the annular sealing members, respectively.

2. The channel tube coupling structure according to claim 1, wherein a cross sectional area of a flow path at the space between an outer peripheral surface of the channel tube and the coupling hole is larger than a cross sectional area of each of the tubes formed within the channel tube.

3. The channel tube coupling structure according to claim 1, wherein end portion openings of the endoscope side tubes each have an annular groove shape along an entire circumference of an inner peripheral surface of the coupling hole.

4. An outer sheath detachably attachable to an insertion portion of an endoscope to cover the insertion portion, the outer sheath comprising:

at least two ports open at a tip end portion of the outer sheath;

a channel tube extending from the tip end portion through a base end portion of the outer sheath to an exterior, the channel tube having at least two communication channels that respectively communicate with the ports;

at least two side holes that respectively communicate with the communication channels, provided in a base end portion of the channel tube exposed to the exterior, and offset from each other in an axial direction of the channel tube.

5. The outer sheath according to claim 4, further comprising:

a plug closing ends of the communication channels in the base end portion of the channel tube.

6. The outer sheath according to claim 4, wherein the at least two side holes are located at different angular positions about the axial direction of the channel tube.

7. An endoscope having an insertion portion to which an outer sheath having a channel tube can be detachably attached to cover the insertion portion, the endoscope comprising:

a tube connector having a coupling hole configured to receive a base end portion of the channel tube;

at least two communicating holes formed in the tube connector, and having respective openings open at an interior surface of the coupling hole, the openings being offset in an axial direction of the coupling hole;

at least three sealing members that define sealing faces that protrude radially inwardly from the interior surface of the coupling hole, and being located so that each of the communicating holes is located between adjacent two of the three sealing members in the axial direction.

8. The endoscope according to claim 7, wherein each of the openings comprises an annular groove.

9. The endoscope according to claim 7, further comprising:

a fastening pipe threadingly engaged with the tube connector and pressingly contactable with a foremost one of the sealing members.

10. The endoscope according to claim 7, wherein the communicating holes are located at different angular positions about the axial direction of the channel tube.

* * * * *